(12) United States Patent  
Scoville et al.

(10) Patent No.: US 7,089,803 B1  
(45) Date of Patent: Aug. 15, 2006

(54) PANEL PERFORMANCE TESTING SYSTEM

(75) Inventors: Christopher R. Scoville, Carnesville, GA (US); Jianhua Pu, Bishop, GA (US)

(73) Assignee: Huber Engineered Woods LLC, Charlotte, NC (US)

(*) Notice: Subject to any disclaimer, the term of this patent is extended or adjusted under 35 U.S.C. 154(b) by 0 days.

(21) Appl. No.: 11/260,180

(22) Filed: Oct. 28, 2005

(51) Int. Cl.  
*G01N 3/02* (2006.01)

(52) U.S. Cl. ......................................................... 73/856

(58) Field of Classification Search ...................... None  
See application file for complete search history.

(56) References Cited

U.S. PATENT DOCUMENTS

| | | | |
|---|---|---|---|
| 2,670,624 | A | 3/1954 | Faris, Jr. et al. |
| 4,420,053 | A | 12/1983 | Russo |
| 4,666,004 | A | 5/1987 | Raz |
| 4,838,085 | A | 6/1989 | Pellerin et al. |
| 4,899,840 | A | 2/1990 | Boubille |
| 5,060,516 | A | 10/1991 | Lau et al. |
| 5,187,987 | A | 2/1993 | Anderson et al. |
| 5,417,536 | A | 5/1995 | Cech |
| 5,431,061 | A | 7/1995 | Bertelsen et al. |
| 5,503,024 | A | 4/1996 | Bechtel |
| 5,666,295 | A | 9/1997 | Bruns |
| 5,739,478 | A | 4/1998 | Zefira |
| 5,922,998 | A | 7/1999 | Zefira |
| 6,053,052 | A | 4/2000 | Starostovic |
| 6,055,867 | A | 5/2000 | Dunne et al. |
| 6,234,497 | B1 | 5/2001 | Stahler, Sr. |
| 6,381,546 | B1* | 4/2002 | Starostovic .................. 702/36 |
| 6,505,129 | B1 | 1/2003 | Starostovic et al. |
| 6,600,111 | B1 | 7/2003 | Simons |
| 2002/0170360 | A1 | 11/2002 | Anand et al. |

OTHER PUBLICATIONS

"Standard Specification for Evaluation of Duration of Load and Creep Effects of Wood and Wood-Based Products", ASTM Std. Designation D 6815-02a, Nov. 2002, pp. 1-11, ASTM International, West Conshohocken PA, U.S.A.

* cited by examiner

*Primary Examiner*—Max Noori  
*Assistant Examiner*—Octavia Davis  
(74) *Attorney, Agent, or Firm*—Raymond Hoch; Carlos Nieves; Patricia Ades

(57) ABSTRACT

A panel performance testing system and method of use is provided for evaluating creep and duration of load (DOL) performance of products, particularly wood-based panels, subjected to bending stress. The panel performance testing system comprises a panel testing support frame assembly; a loading head assembly for applying test load to a panel face; a load transfer assembly for transferring load force from a dead weight to the loading head assembly; a panel deflection sensor; and a mobile loading platform assembly for vertically positioning and supporting dead weight loads, controlling the rate of load transfer of the dead weight loads from the loading platform assembly to the loading head assembly, and an integrated data acquisition system that automatically records and processes the related testing data for the entire course of the testing.

20 Claims, 9 Drawing Sheets

PANEL PERFORMANCE TESTING SYSTEM

FIELD OF THE INVENTION

This invention relates to a system for testing time-dependent mechanical properties of visco-elastic materials such as panel or lumber products, and particularly a system for measuring the creep and duration of load (DOL) responses of the panels or lumbers under bending.

BACKGROUND OF THE INVENTION

An increasing demand exists for pre-fabricated structural panel materials, such as plywood, wafer board, oriented strand board, plaster board, composites of veneer and of wood-based layers, and so forth. These structural materials are heavily used, for instance, in the construction and manufacturing industries. Suppliers and users of these products often need to know their design values or capacities to assist them in making a proper material selection. For instance, among other tests, specimen or control panels cut from large panels or pulled from a given production lot or product type is tested to determine the major mechanical properties of the panel material.

In the case of many viscoelastic materials, such as wood composite products, the loading rate, in pounds/minute or inches/minute of tests is carefully prescribed to allow the comparison of test results from different machines, dates, and test labs. In general, as the loading rate increases, there will be an increase in the apparent strength of the material being tested. This is mainly from the time-dependant response of the viscous portion of the material. A fully elastic material should not exhibit any changes from loading rate to the same magnitude as that of a viscoelastic material.

In the testing of wood composite panel products, the long-term performance of structural panels is important to allow the designers to get a feel for the time-dependant increase in deflection, or creep, that most products exhibit. "Creep" is the name given to the time-dependant increase in deflection that most viscoelastic materials exhibit under sustained loading. In the same time, its strength must be adjusted for the intended load duration. Creep behavior in wood products can often be seen in old bookshelves: after many years with the constant weight of books on the shelves, they tend to sag. In the ASTM Standard for creep testing of wood products, i.e., ASTM D6815-02a, *Standard Specification for Evaluation of Duration of Load and Creep Effects of Wood and Wood-Based Products*, ASTM Int'l, West Conshohocken, Pa., U.S.A., a 12 inch×40 inch piece of wood panel is loaded in "third-point" bending for 90 days in a controlled constant temperature and humidity environment. During the 90 day load period, a constant load is applied, normally by hanging a known weight on a cable that is attached to the loading head, which transfers the load to the wood panel specimen. The test starts with matched sets of panels, some of which are loaded in static bending, to failure at around 5 minute duration. The load rate is approximately 0.035 inch/min. The 5th percentile of the failure stress is calculated from the short-term (5 minute) testing results. The 90-day testing specimens are loaded to the same stress level as prescribed in the testing standard, and they have to be loaded at the same loading rate as the short-term bending tests. This restriction is in place so that the test operators will not knowingly or unknowingly change the loading rate from the rate of the short-term test.

Under certain protocols of ASTM D6815-02a, the load has to be applied very precisely in order to make accurate engineering extrapolations regarding board performance. Wood composite boards typically are viscoelastic materials. As a consequence, the strength of the material changes if the loading rates are different. This load application has most commonly been done by applying the load very slowly, which allows more precision and control over how the load is applied.

In order to strive for such a slow initial loading rate, many varied approaches have been explored. Many years ago, technicians applied the load using a piece of lumber held at each end by two people. These two people would try to slowly lower the weight manually until it hangs from the cable to transfer the load to the specimen. This was not very exact, so other approaches were developed. One approach was to divide the amount of total weight being applied into many smaller separate weights which were loaded on the cable one at a time until the desired aggregate load is provided. These weights could be placed in an intermittent timed manner into a bucket attached to the cable, thereby arriving at the full amount of load in the time prescribed by the ASTM standard. The problem with this additive approach was that the load was not transferred very smoothly to the cable, or in other words, it was more of a step function loading. Another technique has involved placing a screw jack under the load or airbags, and slowly lowering the weight. In some locations, a motor-driven pulley was developed to lower the weight at a certain rate. The system using a motor-drive pulley had the disadvantage of the need to hang another cable to the weight stack, and having to unhook it from each weight stack before moving to the next specimen that needs to be loaded. This added step might introduce some error to the data collection as well as take longer to apply load to many test panel samples. An added disadvantage of the overhead pulley system is that it is larger and more cumbersome to maneuver in tight areas between rows of creep test frames. As a result, engineering extrapolations often are not reliable, and the panel must be "over-engineered" to insure an adequate margin of performance capability.

Prior panel performance testing systems are known which combine panel support, load application, and system control means as an integrated single system positioned at a fixed location for testing panels one-at-a-time. Some panel bending tests, such as creep testing, may require load/deflection testing and data acquisition that lasts extended periods of time. For instance, a constant stress period of 90 days (or even longer for non-decreasing creep rate instances) is stipulated in ASTM D6815-02a.

U.S. Pat. No. 6,053,052 describes a performance testing system for wood-based panels. The testing includes performance of a material under a load concentrated in a single area, performance of edge support systems under a concentrated load and performance of a material under static bending conditions. The system is computerized and automatically applies a load to a panel to be tested using a hydraulically actuated system supported on the panel support frame. The system reads and records deflection of the panel, and provides a printed test report. U.S. Pat. No. 5,187,987 describes a bending beam creep test device in which the test specimen and lower part of a loading mechanism are submerged in a constant temperature liquid coolant. The specimen is supported on two spaced apart support members and a loading head actuated by an air bearing/pneumatic piston mechanism engages the specimen midway between the support members. The deflection of the specimen is measured with a linear variable differential transformer and the load imparted to the specimen by a load cell provided under at least one of the specimen support members.

A panel performance testing device which can be operated on-site that provides accurate and repeatable creep and DOL performance and facilitates concurrent testing of a plurality of test panels would be highly desirable and useful.

SUMMARY OF THE INVENTION

The above needs are met and other advantages and benefits are achieved by the present invention in which a unique panel performance testing system is provided for evaluating the creep and duration of load (DOL) performance of products, particularly wood-based panels, subjected to bending stress.

In one embodiment, a panel performance system is provided comprising a panel testing support frame assembly; a loading head assembly for applying test load to a panel face; a panel deflection sensor; a load transfer assembly for transferring load force from a dead weight to the loading head assembly; a mobile loading platform assembly for vertically positioning and supporting dead weight loads, controlling the rate of load transfer of the dead weight loads from the loading platform assembly to the loading head assembly, and recording and evaluating test data for generation of test results relevant to bending properties, such as creep, of the test panel.

The panel testing support frame assembly includes first and second retaining assemblies for releasably retaining opposite end portions of a test panel in fixed position during a test cycle. In one embodiment, a test panel is retained in an upright orientation in the testing frame with the major length of the panel oriented vertically. The testing support frame assembly, or a plurality of separate frame assemblies, may be placed in fixed location(s) within a testing facility or room in a controlled environment, such as a room maintained at a controlled room temperature and relative humidity.

The loading head assembly is operable to impart a load to a first major face of a test panel between the retained opposite end portions of the panel. In one particular embodiment, the loading head assembly comprises two rectilinear contact rods for applying load to the first major face of a test panel along two parallel lines of contact made by the respective rods along their lengths with the first major panel face, particularly wherein the rods are spaced apart a distance of about one-third the total span of the panel from the retained end portions to provide a three-point bending system.

The panel deflection sensor is included for measuring magnitude of deflection of the panel from an applied load and generating a signal indicative of the magnitude of panel deflection. In a particular embodiment, the deflection sensor is operable to output a signal indicative of panel deflection that is received at the computerized control system via wireless communication. In another particular embodiment, the panel deflection sensor comprises an end portion supporting a deflection sensor, wherein the end portion being movable between a non-testing position where the sensor is out of contact with the panel and a test position where the sensor is in contact with the panel when the deflection sensor is in the test position operable to measure a deflection of the panel.

The load transfer assembly is operable to mechanically couple at least one dead weight to the loading head assembly for load transfer therebetween. In one particular embodiment, the load transfer assembly comprises a pulley and cable, in combination, wherein the cable is operable for connecting the loading head assembly and dead weight and the pulley includes a freely rotatable surface over which the cable may translate in a guided manner.

The mobile loading platform assembly comprises a reciprocally vertically-movable platform for supporting the at least one dead weight; a linear actuator assembly comprising a motor controller and a linear actuator having an output shaft mechanically coupled to the platform, operable for imparting a controlled rate of vertical movement of the platform; a load cell for developing and transmitting load-indicating signals corresponding to amount of weight of the dead weight supported by the platform; and a computerized control system.

In one particular embodiment, the linear actuator comprises a roller screw and rolling elements operably connected to a rotary power transmission source and the output shaft. The linear actuator may comprise, for example, multiple threaded helical rollers assembled in a planetary arrangement around a portion of the output shaft comprising a threaded shaft, wherein the linear actuator converts rotary motion into linear movement of the threaded shaft. A constant power transmission source is provided to power the linear actuator (e.g., a D.C. servomotor, a D.C. stepper motor, and a constant torque A.C. motor). A motor controller, such as a processing card associated with an actuator motor, controls the rate of linear movement of the output shaft of the linear actuator. The linear actuator assembly has a position feedback assembly operable to generate signals corresponding to the position and velocity of the output shaft of the linear actuator. These signals are received and processed by the motor controller in real-time. The motor controller can maintain and, if needed, appropriately adjust the rate of output shaft movement via motor control, to ensure a constant rate of load transfer is maintained. The linear actuator assembly is mechanically coupled with the load-supporting platform such that it can lower the load-supporting platform during initial loading at a rate providing smooth transfer of weight from the platform to the load transfer assembly and hence the loading head. The linear actuator assembly is used to provide vertically movement (e.g., descent) of the platform at a controlled rate effective to load the cable component at a smooth, uniform rate with a progressively increasing amount of weight of the dead weight until the dead weight is fully suspended from the load transfer assembly, such as a cable component of a cable/pulley assembly, and no longer supported in any amount by the platform of the mobile loading platform assembly. In one particular embodiment, the motor controller is operable to control the rate of weight loading to a constant value between 0.005 to 5 inch per minute until the weight is fully suspended from the cable and unsupported by the platform. Among other contributed advantages, this inventive arrangement can eliminate testing error which may be associated with use of a hydraulic drive system for applying load in panel testing devices, which in turn provides more accurate and less variable results.

The computerized control system, amongst other functions, is operable to start and stop movement of the output shaft of the linear actuator via communication with its motor controller. The computerized control system is operable to send a "start" command to the motor controller of the linear actuator together with instructions on a target or specified rate of movement to be provided at the actuator output shaft. The motor controller handles dynamic control of the rate of shaft movement during the cable loading phase with reference to the target value supplied by the computerized control system. Once full load transfer to the cable component is sensed, the computerized control system is operable to send a stop command to the motor controller to discontinue output shaft motion. The computerized control system also receives and stores the panel deflection signals and platform load-indicating signals and corresponding measurement times during initial loading of the cable with the dead weight and during constant load conditions maintained thereafter for a period of time. For example, the computerized control system is operable to receive dead weight data from the load cell(s) placed in the platform, such that the system can instantaneously detect when the dead weight has been fully transferred to the cable component, so that an accurate "zero time" for creep evaluation is identified and stored by the system and also a "stop" command is sent by it to the motor controller to stop further descent of the platform. The computerized control system particularly may include at least one input device and a central processing unit (CPU), and the computerized control system is operable for storing and executing a load/deflection measuring program developed for performing a creep test on a panel.

In a particular embodiment, the computerized control system is operatively coupled to i) the motor controller for controlling starting and stopping translation of the output shaft of the linear actuator, and ii) the load cell and deflection sensor for receiving, recording and processing data relating to the applied load and the corresponding panel deflection, respectively, as a function of time during a cable loading period and a subsequent creep cycle testing period, and the computerized control system being operable to process the recorded test data to compute a measure of the creep rate of the panel. The panel performance system may further comprise a computer monitor coupled in communication with the computerized control system, which is operable to display panel test results.

In one particular embodiment, the mobile loading platform assembly comprises a lift truck frame supporting the platform, the linear actuator, the computerized control system, and wheels for controlled movement of the lift truck frame towards and away from the test panel support frame. In this mobile configuration, the mobile loading platform assembly unit of the panel testing system only needs to be physically present at a given panel testing station for the initial loading stage of a panel creep test. Once loading to full stress load is achieved on a first test panel supported on a first test frame at a first test station using the mobile loading frame, the mobile loading frame can be redeployed for instituting initial loading of another test panel on another support frame at another test station. In this manner, the loading frame and its associated components need not be physically stationed at one given test station over the entire course of a load/deflection test period, such as a 90 day constant stress period of a creep test cycle, for each panel being tested. Instead, the mobile frame can be efficiently used to initially load a plurality of test panels supported on a plurality of associated test frames at different test stations at a testing facility.

The present invention also provides a method for load testing a panel of material using the above-introduced panel performance testing system comprising the steps of immobilizing opposite end portions of a test panel in the panel testing support frame with the retaining assemblies; powering the linear actuator via control of the computerized control system to load the load transfer assembly, for example, a cable component of a cable/pulley assembly, at a uniform rate with a progressively increasing amount of weight of the dead weight until the dead weight is fully suspended from the cable and unsupported by the platform of the mobile loading platform assembly; maintaining, after the powering step, the test panel under constant load for a given time period; acquiring, during the powering and maintaining steps, panel deflection signals and platform load-indicating signals and corresponding measurement times at the computerized control system; and processing, at the computerized control system, the load-indicating signals and the deflection-indicating signals to derive test results comprising the deflection of the panel at applied load and corresponding measurement times. The test results may be saved in a data file format in the computerized control system. The acquired test data may be processed by the computerized control system whereby test results particularly may be generated in the form of one or more of creep rate, load v. deflection during the loading phase, deflection over time, and relative creep, and so forth. The test results may be displayed on a computer monitor and/or stored in a printable format. The method may be used to measuring panel creep rate in accordance with ASTM D6815-02a.

In another embodiment, there is a method of implementing a panel performance testing system encompassing multiple panel testing stations by initially loading a plurality of different test panels supported on different respective test frames at different respective test stations located in the same test room by shuttling the same mobile platform assembly to successive different test stations after completing initial loading and while being absent during the constant stress portion of a creep test cycle as performed on a test panel at a previous test station. In this manner, the mobile platform assembly and associated components need not be dedicated to any given test station, and instead can be used to support a plurality of test stations at a given test facility, which improves testing efficiency and reduces equipment costs.

The inventive panel performance testing system is relatively inexpensive and simple to build. Among other advantages, the panel performance testing system, and its method of use, according to embodiments of the present invention allow weight to be transferred to a test panel specimen during the initial (pre-constant stress) loading stage as a relatively smooth, continuous (and non-stepped) loading function within a relatively short period of time, e.g., less than about ten minutes. Moreover, weight is transferred to the test specimen during the initial loading stage without altering or disturbing the intrinsic macro- or micro-structure of the viscoelastic specimen. The mobile loading platform assembly is a portable unit that allows creep testing to be conducted with very accurate application and recording of the load at the correct rate; The inventive panel performance testing system has many advantages over other panel bending systems including, for example, that the weight can be calibrated or adjusted on the platform before hanging it on the creep test specimen. Also, a seamless connection is provided between the ramp loading phase and the constant (dead weight) phase. That is, it also allows for precise identification and recording of the "zero-time" demarcating the transition from initial loading to a constant stress stage of the test cycle, which increases the accuracy, repeatability, and reliability of the test results. Also, the loading rate can be very exact, and the load-deflection curve can be recorded onto a computer system and saved in a common data file format. Additionally, the modified lift truck is very compact and maneuverable, easy to move in confined spaces, for example, in narrow hallways of creep testing rooms. The mobile loading platform assembly also has the capability to calibrate the cable/pulley system with a separate load cell. Also, in the past, separate programs had to be written to control and record data for each of the three portions of the creep test: Loading, constant load, and unloading and recovery phases. The inventive system allows the user to load and unload at any time at the correct loading rate, while the data acquisition system monitors the deflection.

Additionally, the mobile loading platform assembly is a compact, maneuverable apparatus effective to help maximize the number of panel samples that can be loaded and concurrently tested at neighboring test stations in the minimal amount of space, since that space must be temperature and humidity controlled to conduct creep tests. The panel performance testing system also is conducive for comparative testing and problem solving. For instance, studies of the affects of varying a load rate and/or load amount on a given type of test panel can be efficiently implemented using the inventive panel testing system and methodology, such as by initially loading a plurality of different test panels supported on different test frames at different test stations located in the same test room in rapid succession by shuttling the same mobile loading platform assembly between each test station.

Other features and advantages of the invention will become apparent to those skilled in the art upon review of the following detailed description and drawings.

The figures and elements therein are not necessarily drawn to scale. Similarly numbered elements in different figures represent like features unless indicated otherwise.

DETAILED DESCRIPTION OF THE INVENTION

Figure 1:
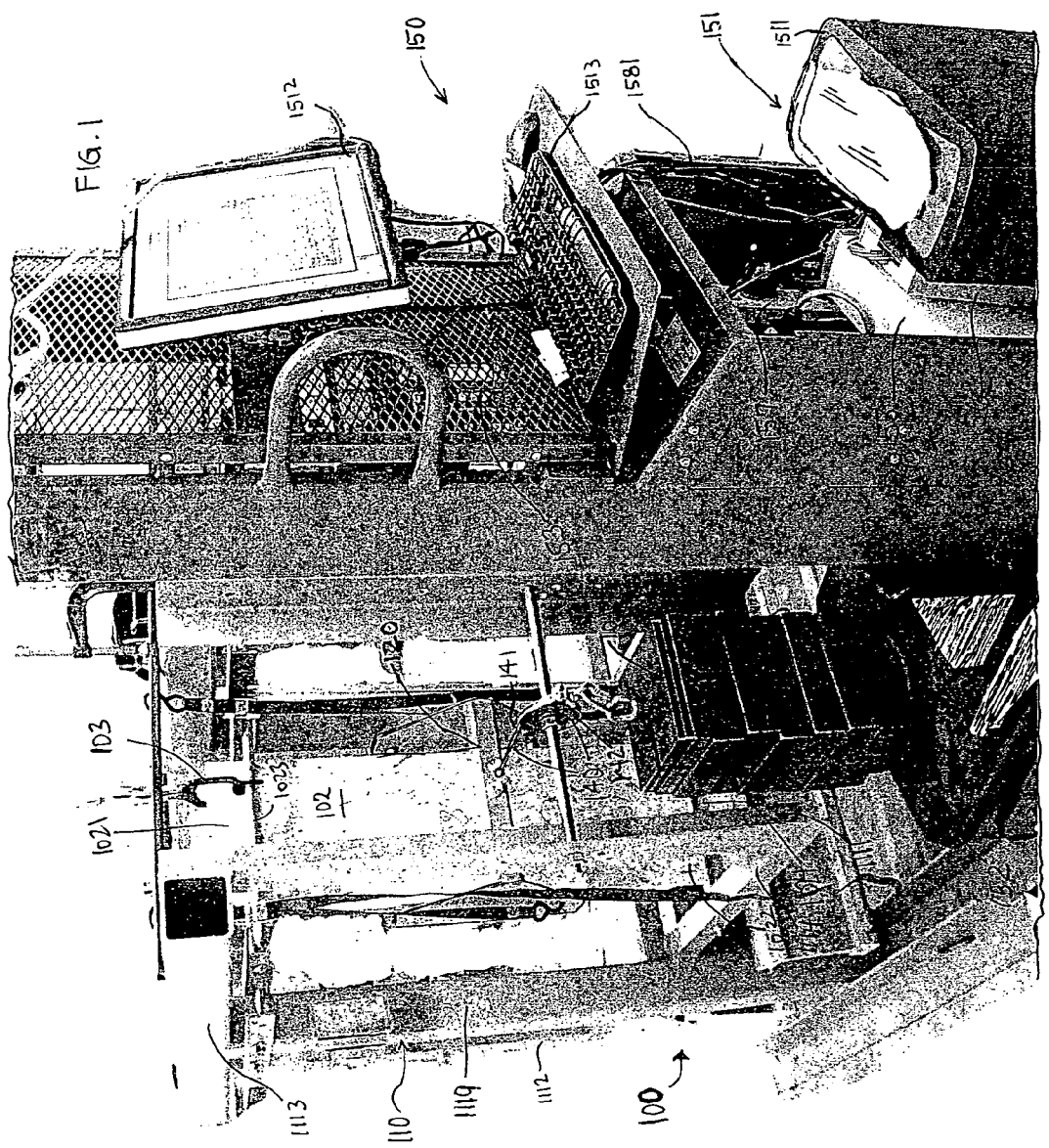
FIG. 1 is a partial perspective view of a panel performance testing system according to an embodiment of the invention.

Referring to FIG. 1, a panel performance testing system 100 is shown that induces deflection of a panel to determine creep or other bending properties of the panel. The testing system 100 includes a panel testing support frame assembly 110; a loading head assembly 120 for applying test load to a panel face of a test panel 102; a panel deflection sensor 130, which is hidden from view at the rear side of panel 102 in FIG. 1, but is shown in FIG. 8; a load transfer assembly 140 for transferring load force from a dead weight 101 to the loading head assembly 120; a mobile loading platform assembly 150 for vertically positioning and supporting dead weight loads 101, controlling the rate of load transfer of the dead weight loads 101 from the loading platform assembly 150 to the loading head assembly 120, and recording and evaluating test data for generation of test results relevant to bending properties, such as creep, of the test panel 102.

As used herein, the term "panel" refers to any viscoelastic structural material, particularly engineered wood panels and raw lumber panels, and more particularly wood-based composite structural panel materials such as oriented strand board (OSB), plywood, wafer board, and the like. The wood-based panels typically, but not exclusively, are manufactured in the form of a generally flat, rectangular-faced or square-faced piece. Rectangular panel pieces may be dimensioned, for example, as about two to about five feet in width and about three to about eight feet in length. Thickness may vary depending on the panel construction and intended application, but may range, for example, from about 0.125 inch to about 2 inches. The wood-based panels that may be measured on the inventive system may have a wide variety of possible end-uses, such as building construction materials, including, for example, roofing panels, wall panels, and flooring or subflooring panels or sheathing, and the like. In the following description of the panel testing system and method of its use, panel testing is carried out at atmospheric pressure and controlled room temperature and humidity conditions unless otherwise indicated.

Figure 8:
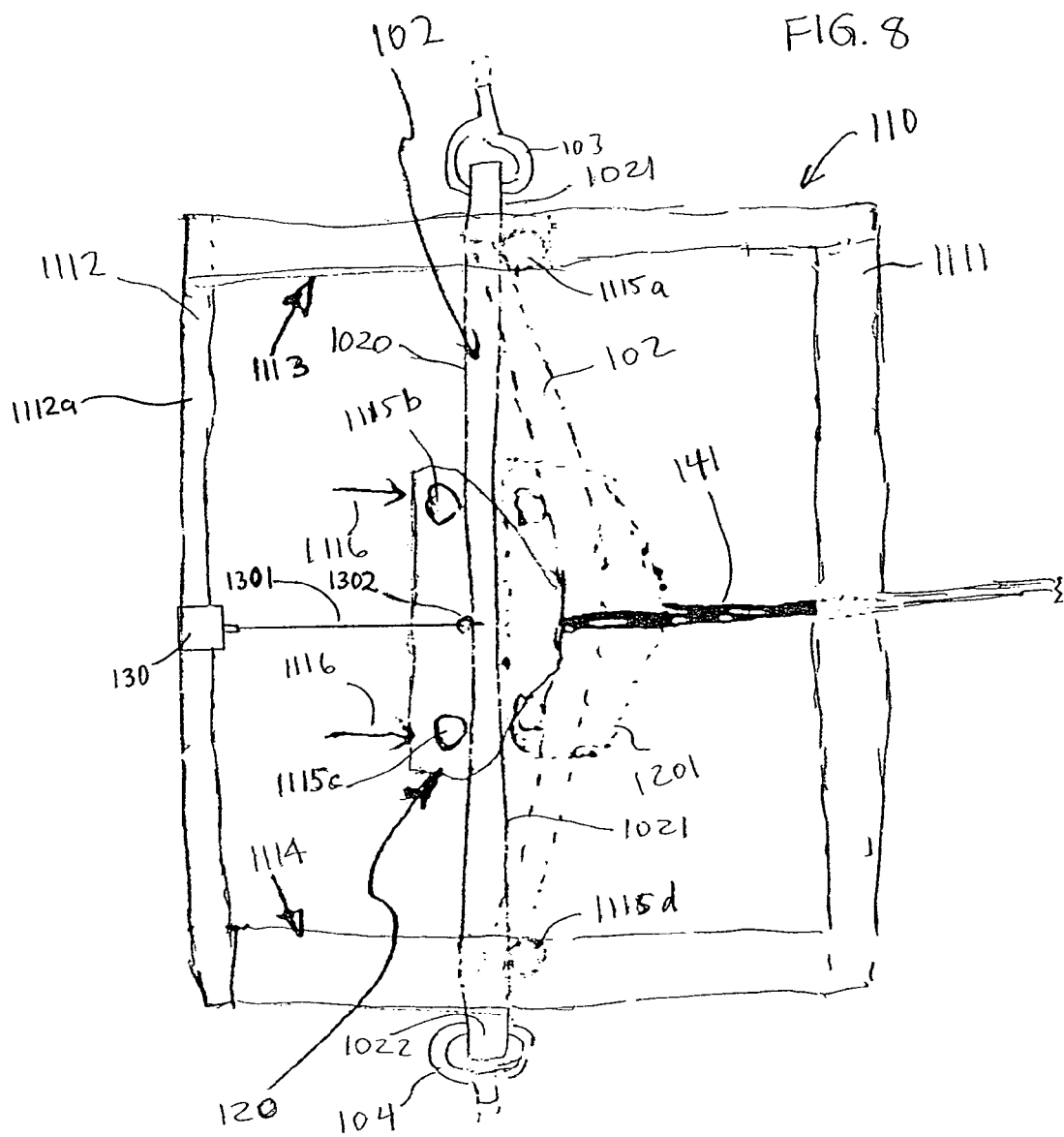
FIG. 8 is an enlarged side view of the loading head assembly and support frame components of the panel performance testing system of FIG. 1, wherein displacement of the loading head assembly and deflection of the retained panel, when placed under load via the cable component, are indicated in dashed lines.

Referring to FIGS. 1 and 8, the panel testing support frame assembly 110 includes first and second retaining assemblies 103, 104 for releasably retaining opposite end portions 1021, 1022 of the test panel 102 in fixed position during a test cycle. The support frame assembly 110 includes a pair of upright, spaced apart front posts or front columns 1111, a plurality of upright, spaced apart rear posts 1112 including a pair of opposite rear side upright posts and an intervening medial upright post 1112a located approximately midway between the rear side upright posts and behind face 1020 of panel 102, and horizontal upper and lower bracket support sections 1113 and 1114 connecting the ends of upright posts. As best seen in FIG. 1, medial upright posts 1119 also may be provided on opposite lateral sides of the test frame assembly 110 approximately midway between the front and rear side upright posts for additional structural frame robustness. The panel retaining assemblies 103, 104 are clamping assemblies comprising C-shaped clamps in this illustration. Each C-shaped clamp is used in combination with a respective forward restraint rod 1023, 1024 which prevents the end portions of the panel 102 from bending forward during load application to the test panel 102. In this illustration, the test panel 102 is retained in an upright orientation in the testing frame assembly 110 with the major length of the panel oriented vertically. In FIG. 1, displacement of the loading head assembly 120 and deflection of the retained panel 102 along direction 1116, when placed under load via the cable component 141, are indicated in dashed lines. The testing support frame assembly, or a plurality of separate frame assemblies, may be placed in fixed location(s) within a testing facility or room in a controlled environment, such as a room maintained at a controlled room temperature and humidity.

Figure 9:
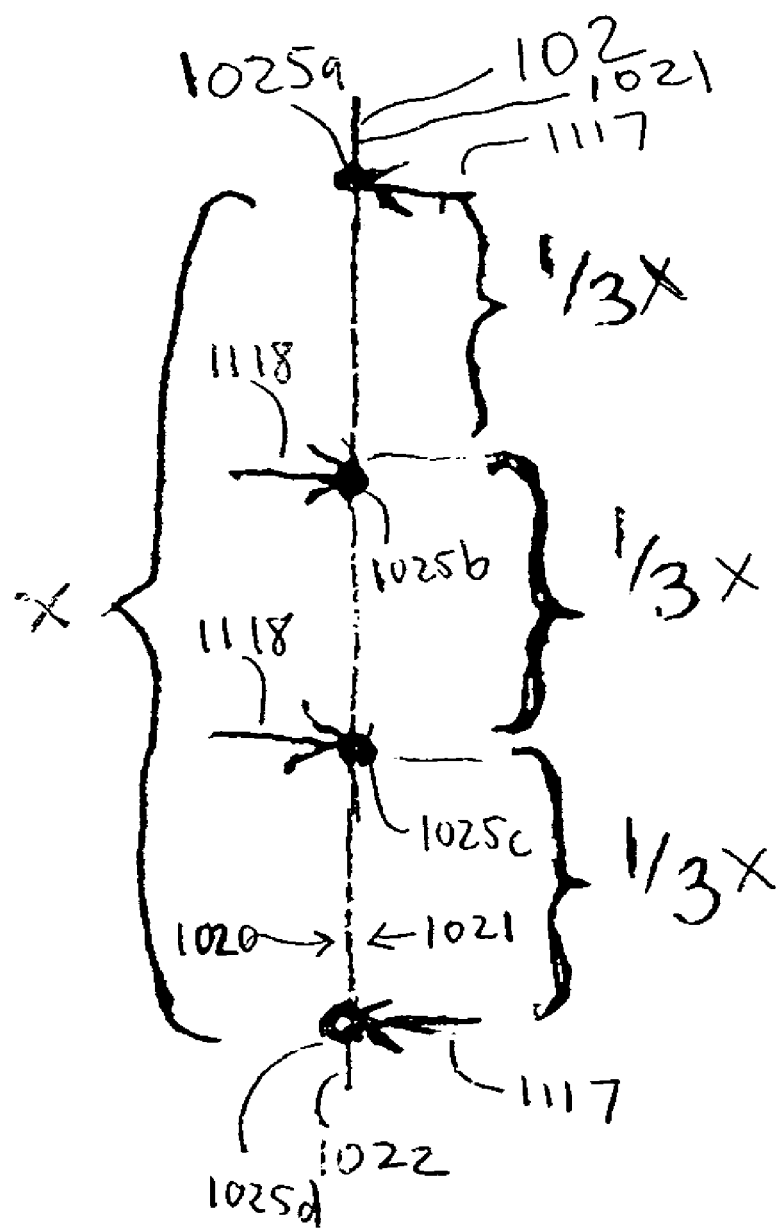
FIG. 9 is a schematic view of a third-point loading configuration applied to a panel specimen on the panel performance testing system of FIG. 1.

Still referring to FIGS. 1 and 8, a major face 1021 of the panel 102 is pinned at the opposite upper and lower ends 1021 and 1022 thereof against rods 1115*a* and 1115*d*, which are rigidly attached to the frame assembly 110. A loading head assembly 120 is operable to impart a load to a major face 1020 opposite to face 1021 of the test panel 102 between the restrained opposite end portions of the panel. In one particular embodiment, the loading head assembly 120 comprises two rectilinear contact rods 115*b* and 115*c* for applying load to the opposite face 1020 of the test panel 102 along two parallel lines of contact made by the respective rods along their lengths with the panel face 1021. As illustrated in more detail in FIGS. 8 and 9, there are 4 points of contact 1025*a* to 1025*d* made between the panel 102 and frame rod 1115*a*, loading assembly rods 1115*b* and 1115*c*, and frame rod 1115*d*, respectively. Rods 1115*a* and 1115*d* generate forces along direction 1117 against face 1021 of panel 102 while rods 1115*b* and 1115*c* generate forces against opposite face 1020 of panel 102 along direction 1118. The four rods 1115*a* to 1115*d* are spaced apart, insofar as neighboring pairs thereof, a distance of about one-third the total span (x) of the panel 102 from the retained end portions to provide a third-point bending system.

Referring to FIG. 8, the panel deflection sensor 130 is supported on rear medial side upright post 1112*a* of support frame 110. For example, the sensor 130 may be bolted or otherwise rigidly connected to post 1112*a* or other suitably located component of support frame 110. The deflection sensor 130 may be, for example, an extension sensor, which includes an extendible/retractable string or cable 1301 that is spooled out or unwound from the sensor 130 from one end and the opposite end thereof is attached to the rear face 1020 of panel 102, such as via a hook 1302 attached to the rear face of the panel 102. For example, the hook may have a threaded screw end that can be manually attached to the panel. The string or cable 1301 moves with board deflection, whereby the sensor 130 quantitatively detects the amount of panel deflection based on the amount of string extension. The sensor 130 is thus used for measuring the magnitude of deflection of the panel as imparted from an applied load at given times. It is operable to generate a signal indicative of the magnitude of panel deflection. In a particular embodiment, the deflection sensor is operable to output a signal indicative of panel deflection that is received at a computer CPU 1511 forming part of a computerized control system 151 via wireless communication (described in more detail infra). The sensor 130 may output the signals as a passive or active mode function. In another particular embodiment, the panel deflection sensor 130 comprises an end portion supporting a deflection sensor, wherein the end portion being movable between a non-testing position where the sensor is out of contact with the panel and a test position where the sensor is in contact with the panel when the deflection sensor is in the test position operable to measure a deflection of the panel. A non-limiting example of a commercially available deflection sensor that may be used in the practice of the present invention is a PT1A-10-UP-500-M6 Extension Sensor, available from Celesco Transducer Products, Inc., Chatsworth, Calif.

The load transfer assembly 140 comprises a cable/pulley assembly 1401 including a cable 141 and a pulley 142 in this illustration, which is operable to mechanically couple at least one dead weight 101 to the loading head assembly 120 for load transfer therebetween. The pulley 142 includes a freely rotatable surface over which the cable 141 may translate in a guided manner.

The mobile loading platform assembly 150 comprises a reciprocally vertically-movable platform 152 for supporting the at least one dead weight 101; a linear actuator assembly 153 operable for imparting a controlled rate of vertical movement of the platform 152; a load cell(s) 154 housed within platform 152, hidden from view in FIG. 1 (e.g., see FIG. 5) for developing and transmitting load-indicating signals corresponding to amount of weight of the dead weight 101 supported by the platform 152; and a computerized control system 151.

Figure 2:
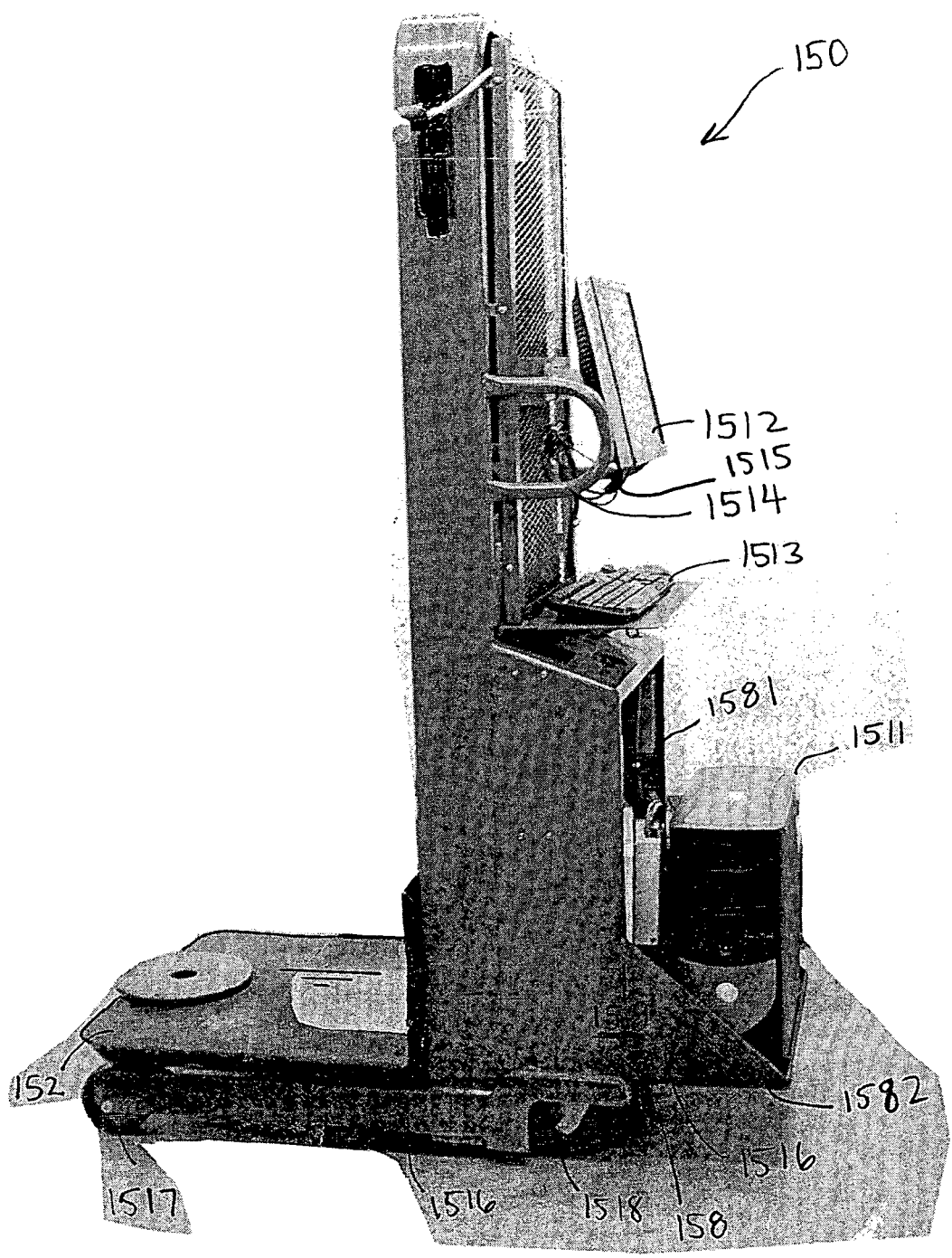
FIG. 2 is perspective view of the mobile loading platform assembly of the panel performance testing system of FIG. 1.
Figure 3:
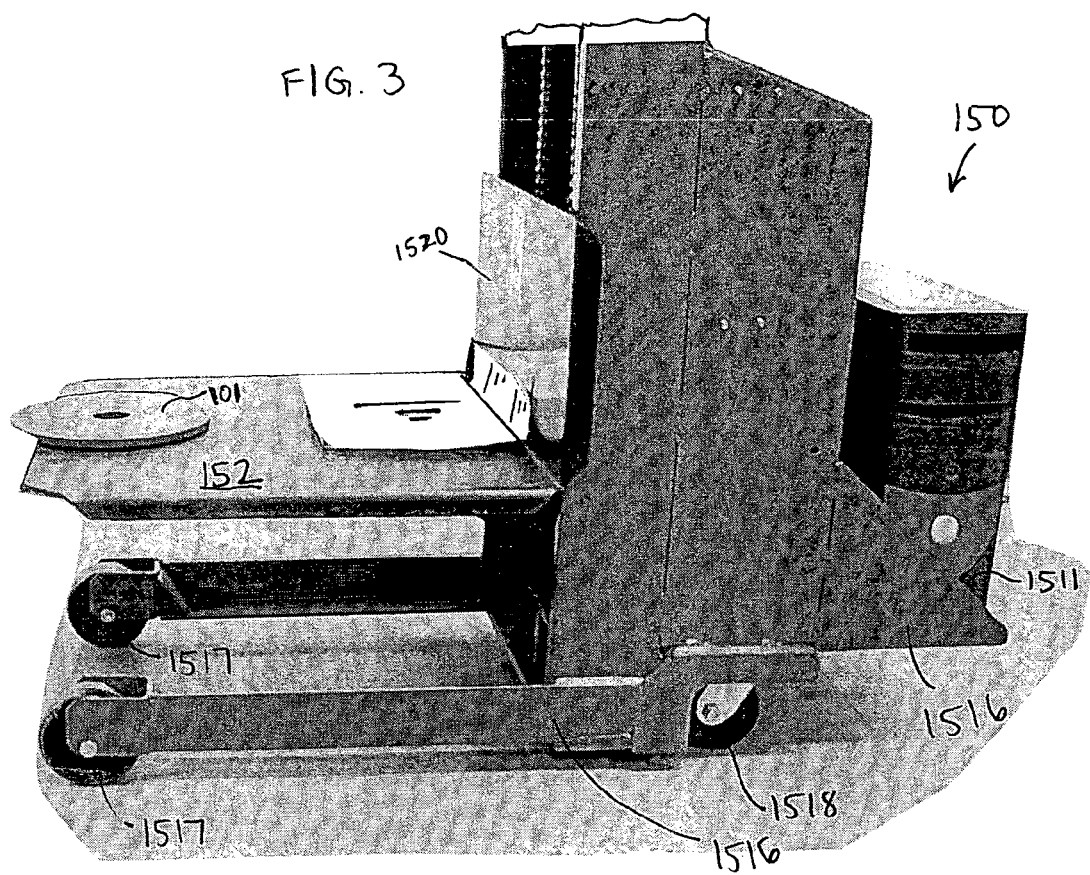
FIG. 3 is a partial perspective view of the mobile loading platform assembly of FIG. 2 with the platform thereof in a partly lifted condition.

Referring to FIGS. 2–3, the mobile loading platform assembly 150 has a body frame 1516 and two pairs of rollers 1517 and 1518 (front and rear locations) rotatably mounted to the undercarriage for providing mobility, in which handlebars 1514, 1515 can be used by an operator to steer and (re-)position the assembly 150. The body frame 1516 includes a box portion 158 including an enclosure portion 1581 and a platform portion 1582. An on board power supply 155, backup power supply/electric power conditioner 156, and a surge protector 157 are stored on board assembly 150 in or on box portion 158, such that they travel with the assembly.

Figure 4:
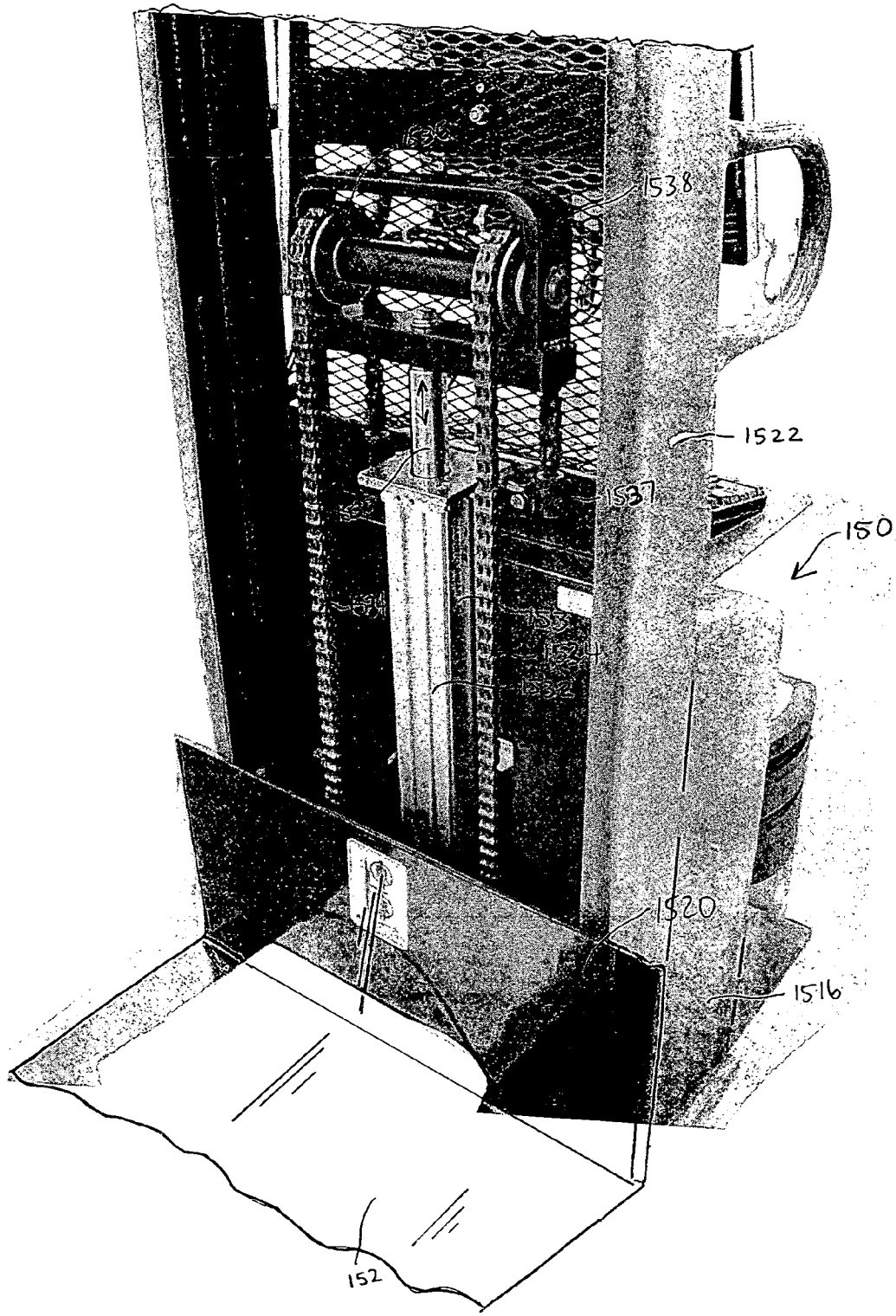
FIG. 4 is a partial perspective view of the linear actuator assembly of the mobile loading platform assembly of FIG. 2.
Figure 5:
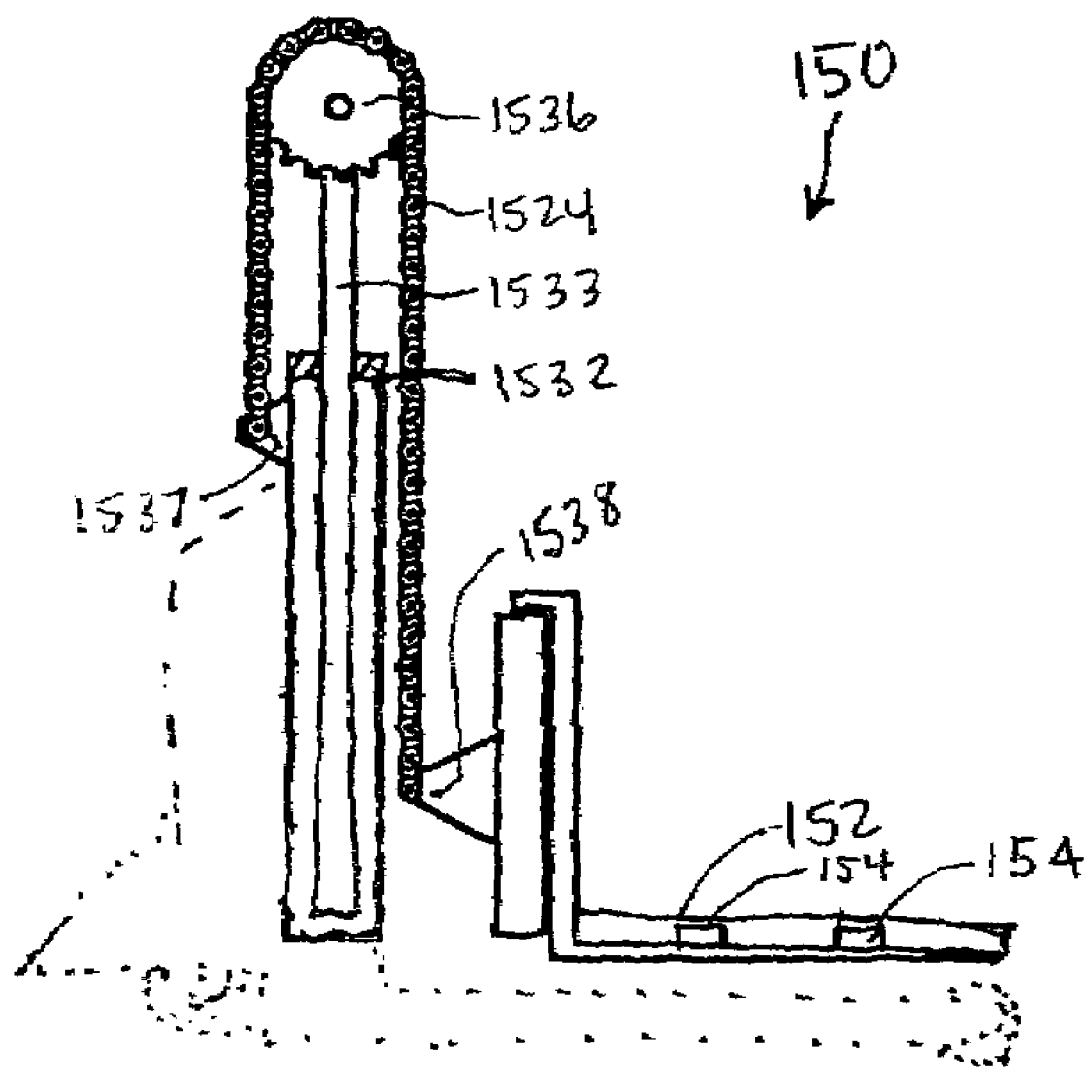
FIG. 5 is a simplified schematic side view of the mobile loading platform assembly of FIG. 2.

Referring to FIGS. 4–5, linear actuator assembly 153 includes a linear actuator 1532, and a motor controller 1531 (see FIG. 7), and having an output shaft 1533 mechanically coupled to the platform 152. An upright bracket 1520, which is integrally attached to lift platform 152 extending perpendicularly thereto, is movably attached frame 1516. Lift-chains 1534 are attached to bracket 1520 and extend over sprockets 1536 which are positioned proximate to one end of a mast structure 1522 forming part of frame 1516, and generally opposite the wheels 1517, 1518. Linear actuator 1532, which houses a vertically movable output shaft 1533, is attached to an upright portion of frame 1516. One end 1537 of each lift-chain 1534 is attached to frame 1516, and the opposite end 1538 is attached to bracket 1520. The output shaft 1533 is connected to a bracket structure 1538 on which the sprockets 1536 are rotatably mounted. The bracket structure 1538 moves vertically in tandem with the output shaft 1533. The movement of output shaft 1533 causes the bracket 1520 to move vertically relative to the mast structure 1522.

Figure 6:
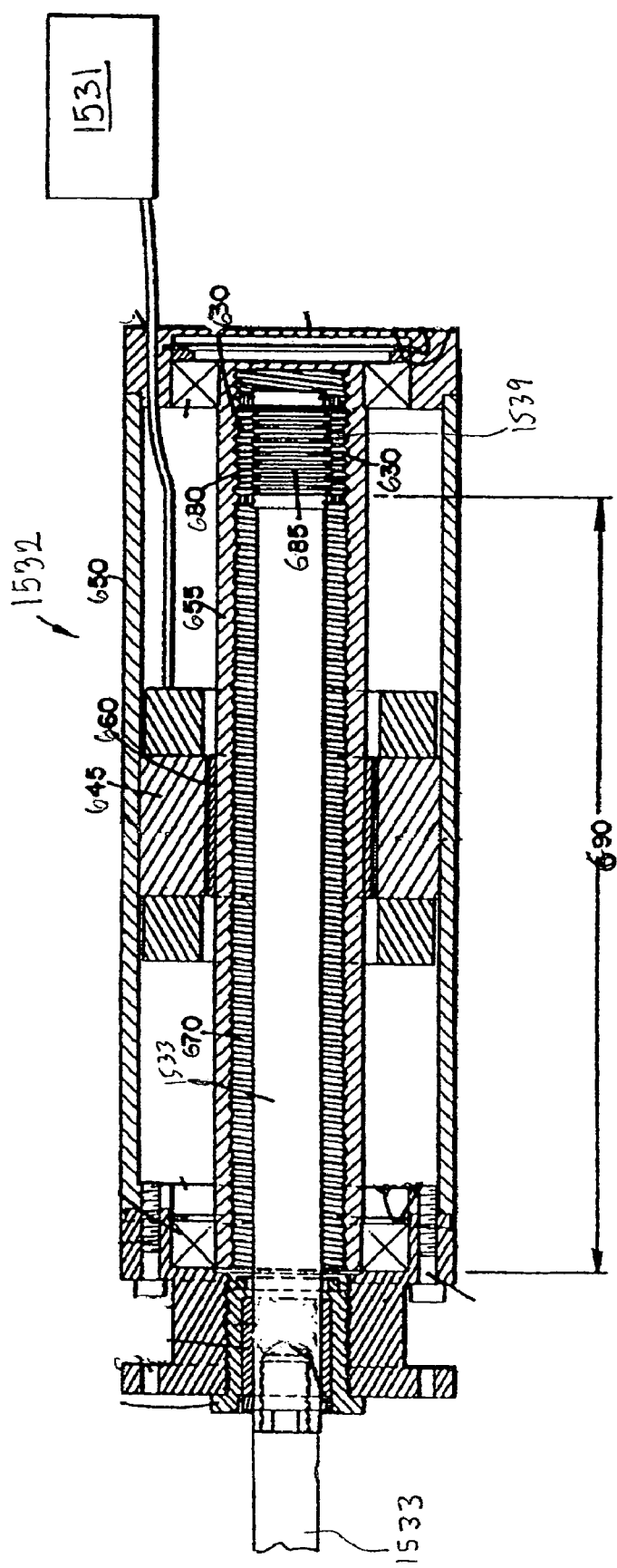
FIG. 6 is a cross-sectional view of the linear actuator component of the linear actuator assembly of FIGS. 4–5.

Referring to FIG. 6, in one particular embodiment, the linear actuator 1532 converts motor power into linear motion of the output shaft 1533. In operation, the output shaft 1533 of the actuator 1532 extends or retracts along a vertical linear line of motion in response to signals provided by the computerized control system 151, which in turn effects vertical movement of platform 152. A constant power transmission is provided to power the linear actuator (e.g., a D.C. servomotor, a D.C. stepper motor, and a constant torque A.C. motor). The above-referenced motor controller 1531, such as a processing card (not shown) associated with an actuator motor, controls the rate of linear movement of the output shaft 1533 of the linear actuator 1532. The linear actuator assembly 153 has a position feedback assembly (not shown) operable to generate signals corresponding to the position and velocity of the output shaft 1533 of the linear actuator 1532. These signals are received and processed by the motor controller 1531 in real-time. The motor controller 1531 can maintain and, if needed, appropriately adjust the rate of output shaft movement via motor control, to ensure a constant rate of load transfer is provided and maintained during the ramp loading phase. The motor controller 1531 operates under start/stop command control of the computerized control system 151, such as via hypertext commands.

Referring still to FIG. 6, the linear actuator 1532 in this illustration converts rotary motion into linear movement of the threaded shaft. Within actuator 1532, multiple threaded helical transmission rollers 630, also referred to herein as planetary rollers, are assembled around the actuator's output shaft 1533 and also follow threads machined on the inside surface of a hollow armature drive cylinder 655. Within actuator 1532, the output shaft 1533 and the armature each provided with a helical thread which mate with the threading of the planetary rollers interposed therebetween and in contact with the armature 655 and the output shaft 1533. The planetary rollers convert a motor's rotary motion into linear movement of the output shaft. Roller screws which incorporate and interact with planetary rollers of this general nature have been described for non-related applications, e.g., see U.S. Pat. No. 4,648,285, which teachings are incorporated herein by reference for all purposes. A non-limiting example of a commercial actuator that can be adapted for use in embodiments of the present invention is an Electrak® 2000 actuator (Warner Electric/Dana Corporation), or an EXLAR GSX series actuator (Control Techniques-Americas LLC, an Emerson Industrial Automation Company, Chanhassen, Minn.). Indexers and drives providing the ability to program and operate the Electrak® 2000 actuator are also commercially available from Warner Electric/Dana Corporation, including in-line programmable motion configurations of the Electrak® 2000 actuator which include an indexer (e.g., part no. SS20001) including motor control programming software (e.g., part no. MS2000), and a drive (e.g., a 12 amp drive: part no. SS2000D12). Parallel drive/actuator configurations also may be used, space permitting in frame 1516.

In more detail, the illustrated linear actuator 1532 includes output shaft 1533, a plurality of transmission rollers 630, and an integral electric motor assembly including stator 645 and housing assembly 650. The motor assembly moves the output shaft 1533 between a retracted position and an extended position and includes an elongated cylinder 655 formed of a magnetic material rotatably supported relative to the housing assembly 650. Magnets 660 are mounted about an outer surface of the cylinders 655 to form an armature with the cylinder 655 within the motor assembly. The stator 645 is attached to and supported by the housing assembly 650 and encircles the cylinder 655. An external motor controller 1531 selectively energizes the stator 645 to rotate the armature clockwise or counter-clockwise. The elongated cylinder 655 includes a central threaded bore 670 the threads of which are engaged by the transmission rollers 630. The output shaft 1533 is coupled with the transmission rollers 630 to move along the threaded bore 670 on rotation of the cylinder 655. Only a smooth surfaced portion of the output shaft extends outside the threaded bore 670. The elongated cylinder 655 forms a drive cylinder within the actuator assembly as well as forming the armature of the motor assembly. Accordingly, the elongated cylinder 655 is referred to herein as the armature drive cylinder. The output shaft 1533 and the transmission rollers 630 are axially aligned within threaded bore 670 of the armature drive cylinder 655. The rings 680 define camming surfaces which are engaged by the threaded bore 670 of armature drive cylinder 655 to move the actuator assembly along the threaded bore 670 in response to the rotation of the armature drive cylinder 655. The extent of the threaded bore 670 within the armature drive cylinder 655 defines a track along which the transmission rollers 630 of the actuator assembly move. A portion 1539 of the output shaft 1533 includes annular rings 685, which are engaged by the annular rings 680 of transmission rollers 630 to advance the output shaft 1533. When the armature drive cylinder 655 is selectively rotated clockwise or counterclockwise by the stator 645, the threaded bore 670 engages the annular rings 680 of the transmission rollers 630 to selectively move the rollers 630 along threaded bore 670. The annular rings 680 of the transmission rollers 630 engages the annular rings 685 of the output shaft portion 1539 to move the output shaft 1533. Other features and components of the actuator assembly include those described in U.S. Pat. No. 5,557,154, which teachings are incorporated herein by reference. A position feedback assembly (not shown) of a conventional design and function is provided operable to generate signals corresponding to the position and velocity of the output shaft of the linear actuator. In operation, the output shaft 1533 of the actuator 1532 extends or retracts along a linear line of motion in response to signals provided by the motor controller 1531. An internal encoder (not shown) of conventional design and function may be included in linear actuator 1532 that communicates with the motor controller 1531 and is operable to instantaneously determine, at a location within the linear actuator 1532, the relative axial position and compute the rate of linear motion of the output shaft 1533.

The linear actuator assembly 153 is used to provide vertically movement (e.g., descent) of the platform 152 at a controlled rate effective to load the cable component 140 at a smooth, uniform rate with a progressively increasing amount of weight of the dead weight 101 until the dead weight 101 is fully suspended from the load transfer assembly 140, such as a cable component 140 of a cable/pulley assembly 1401, and no longer supported in any amount by the platform 152 of the mobile loading platform assembly 150. In one particular embodiment, the motor controller 1531 is operable to control the rate of weight loading to a constant value between 0.005 to 5 inch per minute until the weight 101 is fully suspended from the cable 140 and unsupported by the platform 152. Among other contributed advantages, this linear actuator drive-based approach eliminates testing error associated with use of a hydraulic drive system for controlling load application in panel testing devices, which in turn provides more accurate and less variable results.

The computerized control system 151, amongst other functions, is operable to start and stop movement of the output shaft 1533 of the linear actuator 1532 via communication with its motor controller 1531. The computerized control system 151 is operable to send a "start" command to the motor controller 1531 of the linear actuator 1532 together with instructions on a target or specified rate of movement to be provided at the actuator output shaft 1533. The motor controller 1531 handles dynamic control of the rate of shaft movement during the cable loading phase with reference to the target value supplied by the computerized control system 151. Once full load transfer to the cable component 141 is sensed, the computerized control system 151 is operable to send a stop command to the motor controller 1531 to discontinue output shaft motion. Computerized system 151 also receives and stores the panel deflection signals received from panel deflection sensor 130 and platform load-indicating signals from load cell(s) 154 and corresponding measurement times during initial loading of the cable 141 with the dead weight 101 and during constant load conditions maintained thereafter for a period of time. For example, the computerized control system 151 is operable to receive dead weight data from load cell(s) 154 placed in the platform 152, such that the control system 151 can instantaneously detect when the dead weight 151 has been fully transferred to the cable component 141, so that an accurate "zero time" for creep evaluation is identified and stored by the control system 151 and also a "stop" command is sent by it to the motor controller 1531. The "zero time" is when the stack weight supported by the platform 152 becomes zero, an event which the computerized control system 151 recognizes in real-time as it continuously receives signals from the load cell(s) 154 in the platform 152. As the initial weight of the platform 152 without the stack weight 101 is stored in the computerized control system 151, the system 151 can identify when all the stack weight has been off-loaded onto the cable 141 by a simple mathematical calculation. A processor component of the computerized control system 151 is used to determine when the whole load of the stack weight has been transferred to the cable from the platform. Immediate appropriate transitioning in data measuring occurs at the computerized control system 151 for the constant load phase of the test cycle, while the motor controller 1531 of the linear actuator assembly is sent a stop or stand-down signal from the computerized control system 151 to stop downward descent of the platform 152. The computerized control system 151 particularly may include at least one input device 1513 (e.g., a keyboard) and a central processing unit (1511), and the computerized control system 151 is operable for storing and executing a programmable load/deflection measuring program for performing a creep test on a panel.

Figure 7:
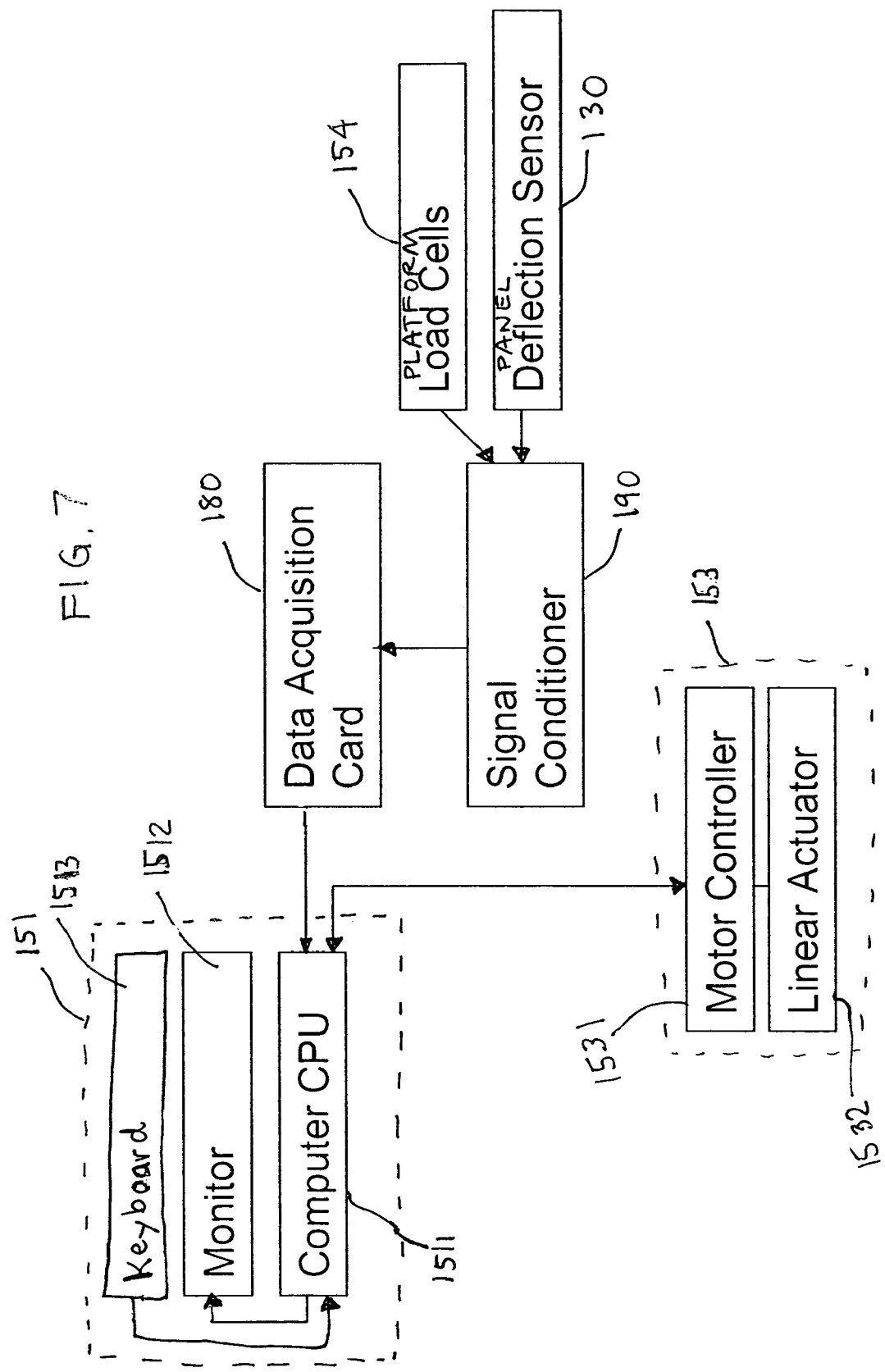
FIG. 7 is a block diagram of the hardware and communication layout suitable for the exemplary system of the panel performance testing system of FIG. 1.

Referring to FIG. 7, the computerized control system 151 includes a computer CPU 1511 that is operatively coupled to i) the motor controller 1531 for controlling starting and stopping translation of the output shaft of the linear actuator 1532, and ii) the load cell(s) 154 and panel deflection sensor 130 for receiving, recording and processing data relating to the applied load and the corresponding panel deflection, respectively, via signal conditioner unit 190 and data acquisition card 180, as a function of time during (1) a cable loading period and (2) during a subsequent creep cycle testing period, and the computer CPU 1511 is operable to process the recorded test data to compute a measure of the creep rate of the panel. The panel performance system may further comprise an on board computer monitor 1512 coupled in communication with the computer CPU 1511, which is operable to display panel test results.

The hardware of computer CPU 1511 may include a central processing unit (CPU), a random access memory (RAM), a read only memory (ROM), and a clock. The computer may be a standard off-the-shelf item having the conventional components, e.g., an IBM compatible computer with 1.0 GHz microprocessor and 256 MB RAM. Signal conditioner unit 190 is an amplifier, D/A converter and interface unit which receives, conditions, converts and passes signals from the load cells 154 and deflection sensor 130, via data acquisition card 180, to the computer CPU 1511 where they are acted upon by a software portion of system 100 fetched from computer RAM and necessary information for system operation from computer ROM. Such data acquisition signal conditioners are available commercially, e.g., National Instruments SCB-68. The RAM contains a conventional operating system, e.g., MS-DOS with a Windows™ environment, both commercially available from Microsoft, Inc., including a system program for loading the software portion (not shown) of the computerized control system 151 into the on board computer 1511. The software portion of the control system 151 is suitably stored in a secondary storage medium, e.g., hard disk, for reading by the computer in a conventional fashion.

The software program of control system 151 includes a load/deflection program suitable for implementing a creep and/or other bending property evaluations on a test panel(s) on the inventive system. The software portion of control system 151 of system 100 in effect controls the computer to perform a number of functions necessary to perform a creep test on a test panel using system 100. The software portion suitably includes a data acquisition and control program. The software program may be implemented in a graphical based software language, such as LABVIEW available from National Instruments Corporation (www.ni.com), which can be operated on a Windows operating platform such as Windows XP. Alternatively, the program may be a software program which operates as a macro in a spreadsheet/graphics program such as Microsoft Excel™. The data acquisition program, responsive to data entry respecting the panel to be tested, controls the linear actuator assembly and application of the load to the panel, and permits signals to be input into the computer from sensors, i.e., load cell 154 and deflection sensor 130, and stores the signals as measured test data records in a test data text file of measured test data. The measured test data are then processed by the software program to provide a graphic representation of the creep rate, which can be displayed on monitor 1512 or provided as a hard copy via a printer (not shown) operatively communicating with the computer CPU 151. The software program also can generate results in tabular summary report form.

In one embodiment, short-term bending (destructive) tests per ASTM D 6815-02a are performed either on the inventive system, or alternatively, on a separate suitable panel bending system, such as a Universal testing machine or similar device, and loading rate in conformance with the ASTM standard is determined. A multiple number of tests panels from a common production run and/or specification also can be used for this step to determine an average value for loading rate. For purposes of this embodiment, based on the failure loads and time to failure determined from the destructive panel tests, then a loading rate and load is calculated for non-destructive, extended duration (90 day) creep tests in accordance with guidelines set forth in ASTM D 6815-02a. Then, non-destructive tests are performed to generate load-deflection data needed to evaluate creep and other mechanical properties of interest of a panel or batch of panels. In this embodiment, the loading rate for the non-destructive tests to attain the pre-selected constant stress level also should conform with guidelines in ASTM D 6815-02a. The inventive system 100 can be used for conducting non-destructive panel tests, and its computerized control system 151 operated to generate data results, on panel creep rate in the constant load phase, and/or other mechanical properties such as relative creep during constant load phase, load versus deflection during the loading phase, and load versus deflection during the loading phase. Also, other mechanical property evaluations may be evaluated on a test panel using the inventive system 100, such as DOL, varied load benchmarking tests, or direct loading using a different weight attachment configuration. A multiple number of test panels of a given production run also can be evaluated non-destructively in this manner, although not required given the accuracy in creep evaluation provided by the inventive system 100.

As illustrated herein, the mobile loading platform assembly generally may comprise a lift truck frame supporting the platform, the linear actuator, the computerized control system, and wheels for controlled movement of the lift truck frame towards and away from the test panel support frame. In this mobile configuration, the mobile loading platform assembly unit of the panel testing system only needs to be physically present at a given panel testing station for the initial loading stage of a panel creep test. Once loading to full stress load is achieved on a first test panel supported on a first test frame at a first test station using the mobile loading frame, the mobile loading frame can be redeployed for instituting initial loading of another test panel on another support frame at another test station. In this manner, the loading frame and its associated components need not be physically stationed at one given test station over the entire course of a creep test period, such as a 90 day constant stress period of a creep test cycle, for each panel being tested. Instead, the mobile frame can be efficiently used to initially load a plurality of test panels supported on a plurality of associated test frames at different test stations at a testing facility.

The present invention also provides a method for load testing a panel of material using the above-introduced panel performance testing system comprising the steps of immobilizing opposite end portions of a test panel in the panel testing support frame with the retaining assemblies; powering the linear actuator assembly via start/stop control of the computerized control system to load the load transfer assembly, for example, a cable component of a cable/pulley assembly, at a uniform rate via the linear actuator assembly motor controller with a progressively increasing amount of weight of the dead weight until the dead weight is fully suspended from the cable and unsupported by the platform of the mobile loading platform assembly; maintaining, after the loading step, the test panel under constant load for a given time period; acquiring, during the loading and maintaining steps, panel deflection signals and platform load-indicating signals and corresponding measurement times at the computerized control system; and processing, at the computerized control system, the load-indicating signals and the deflection-indicating signals to derive test results comprising the deflection of the panel at applied load and corresponding measurement times. The test results may be saved in a data file format in the computerized control system. The acquired test data may be processed by the computerized control system whereby test results particularly may be generated in the form of creep rate. The test results may be displayed on a computer monitor and/or stored in a printable format. The method may be used to measuring panel creep rate in accordance with ASTM D6815-02a.

The panel performance testing system also may be implemented as an arrangement for initially loading a plurality of different test panels supported on different respective test frames at different respective test stations located in the same test room by shuttling the same mobile platform assembly to successive different test stations after completing initial loading and while being absent during the constant stress portion of a creep test cycle as performed on a test panel at a previous test station. In this manner, the mobile platform assembly and associated components need not be dedicated to any given test station, and instead can be used to support a plurality of test stations at a given test facility, which improves testing efficiency and reduces equipment costs.

The inventive panel performance testing system is relatively inexpensive and simple to build. Among other advantages, the panel performance testing system, and its method of use, according to embodiments of the present invention allow weight to be transferred to a test panel specimen during the initial (pre-constant stress) loading stage as a relatively smooth, continuous (and non-stepped) loading function within a relatively short period of time, e.g., less than about ten minutes. Moreover, weight is transferred to the test specimen during the initial loading stage without altering or disturbing the intrinsic macro- or micro-structure of the viscoelastic specimen. The mobile loading platform assembly is a portable unit that allows creep testing to be conducted with very accurate application and recording of the load at the correct rate. The inventive panel performance testing system has many advantages over other panel bending systems including, for example, that the weight can be calibrated or adjusted on the platform before hanging it on the creep test specimen. Also, a seamless connection is provided between the ramp loading phase and the constant (dead weight) phase. That is, it also allows for precise identification and recording of the "zero-time" demarcating the transition from initial loading to a constant stress stage of the test cycle, which increases the accuracy, repeatability, and reliability of the test results. Also, the loading rate can be very exact, and the load-deflection curve can be recorded onto a computer system and saved in a common data file format. Additionally, the modified lift truck is very compact and maneuverable, easy to move in confined spaces, for example, in narrow hallways of creep testing rooms. The mobile loading platform assembly also has the capability to calibrate the cable/pulley system with a separate load cell. Also, in the past, separate programs had to be written to control and record data for each of the three portions of the creep test: loading, constant load, and unloading and recovery phases. The inventive system allows the user to load and unload at any time at the correct loading rate, while the data acquisition system monitors the deflection.

Additionally, the mobile loading platform assembly is a compact, maneuverable apparatus effective to help maximize the number of panel samples that can be loaded and concurrently tested at neighboring test stations in the minimal amount of space, since that space must be temperature and humidity controlled to conduct creep tests. The panel performance testing system also is conducive for comparative testing and problem solving. For instance, studies of the affects of varying a load rate and/or load amount on a given type of test panel can be efficiently implemented using the inventive panel testing system and methodology, such as by initially loading a plurality of different test panels supported on different test frames at different test stations located in the same test room in rapid succession by shuttling the same mobile loading platform assembly between each test station.

EXAMPLE

A lift truck including a lift frame and control panel space supported on rollers, WESCO Industrial Products, Model Number PSPL-60-2424-15S (Part No. 261074), capacity 1500 pounds, load center 15 inch, 24 inch×24 inch platform, was modified by removing the battery and the hydraulic motor and piston assembly. A hole was drilled in the lift platform to allow the bottom of a weight stack bolt to protrude through the platform deck. Three load cells (Omega Engineering LCHD-1K load cells) were installed in the deck and a steel plate was machined to fit onto the load cells, to allow the stack of weights to be supported by the steel plate and allowing the load cells to measure the weight of a stack of weights placed on the steel plate. A linear actuator/stepper motor (Electrak® 2000, Warner Electronic/Dana Corporation) with programmable motion control was installed in place of a hydraulic cylinder on the lift truck. The programmable motion control included a 3-Superior Electric SLO-SYN Motor Type KMT092F-II0, 3.48 Amps; and a 4-Superior Electric SLO-SYN Motor Controller Module, including a Warp Drive XWC External Wiring Card and a Warp Drive SS2000D6i Controller module. The motor controller was installed in the lift truck electrical panel space. An extension was welded onto the back of the electrical box to allow room for a computer CPU (Dell Optiplex GX280 computer, mouse and keyboard) to be installed. A small platform was welded onto the back of the upright to allow for the computer keyboard and mouse to be used. The computer monitor (Dell 17 inch flat screen monitor) was mounted on the back of the upright portion, to allow easy viewing. The computer, and also a power supply (Kepco RKW 12-4.3K power supply), backup power supply/electric power conditioner (APC Back-UPS RS 1500 Power Supply), signal conditioner (National Instruments SCB-68 Data Acquisition Signal Conditioner)), surge protector (Belkin Surgemaster Power Surge Protector), and power switch were installed in the electrical box portion space of the lift truck. The above-identified power supply requires an AC current, which is then converted to a lower voltage specific and clean power supply for the load cells. The above-identified backup power supply/electric power conditioner is designed to work for up to about 45 minutes without being plugged in, and, depending on usage amounts, it needs to be plugged in into a power outlet, etc., at regular intervals. A power cord (not shown) can be used to connect the backup power supply/ electric power conditioner to a utility power outlet or other electric power source. Software (loading test control and data processing protocols in LABVIEW language), wireless card (NETGEAR Wireless card with wireless router) and antenna, and data acquisition card (DAQ) were installed onto the computer. The installation locations of some of the hardware components indicated above is exemplified in FIGS. 1–7, and reference is made thereto. The mobile loading platform, as assembled, has a load capacity of 1500 pounds, and a loading rate of between 0.005 inch/min to 5 inch/min. It was easily movable to-and-from loading positions at separate panel-supporting test frames at separate test stations located in the same environment-controlled test room.

An exemplary method for determining panel creep for a batch of specimen panels that includes use of the mobile loading platform assembly as part of a panel performance testing system, is described herein is as follows:

(A) Perform short-term bending (destructive) tests per ASTM D 6815-02a, such as on the inventive system or on a separate suitable panel bending system, such as a Universal testing machine or similar device, and determine a loading rate in conformance therewith.

(B) To perform the non-destructive tests in accordance with ASTM D 6815-02a, place stack of weights on the load platform of the mobile loading platform assembly. The stack of weights may be easily placed on the loading platform assembly with a small crane or forklift.

(C) Correct stack weight is provided and confirmed. The weight of the stack can be adjusted by adding or subtracting small weights while the stack is on the load platform. The readout on the computer screen tells the operator what the actual weight is.

(D) Raise weight to correct height to hook up the cable. The cable that supports the weight is already attached to the loading head and the panel. The stack of weights will need to be raised sufficiently high to hook up the cable to the weights using the universal link. At this point, the load is ready to be lowered so it is being supported on the panel. The system makes it possible to raise and lower the load platform manually and zero the load.

(E) Data Input: Input sample number and panel dimensions. Specify loading rate (viz., the load rate determined from the short term (destructive) tests), and command the system to initiate loading. The loading rate will be the same as the short-term loading rate for static bending tests. This is typed into the control panel portion of the software for the loading program.

(F) Lower the platform at the correct loading rate. This step is automatically started by the software after the operator clicks on the start button. While loading (i.e., platform is lowered at the selected rate), the load and deflection are monitored and data saved to a file.

(G) At the end of loading when the full weight has been transferred from the loading platform to the cable (i.e., load=0 lbs. on the loading platform), the end of loading is recorded and the beginning of the creep cycle (90 day dead load test) commenced.

(H) Monitoring and recording of the deflection of the wood-based test specimen is continued for 90 days.

(I) Generate creep results via the computerized control system.

While the invention has been particularly described with specific reference to particular process and product embodiments, it will be appreciated that various alterations, modifications and adaptations may be based on the present disclosure, and are intended to be within the spirit and scope of the present invention as defined by the following claims.

What is claimed is:

1. A panel performance testing system, comprising:
a panel testing support frame assembly comprising first and second retaining assemblies for releasably retaining opposite end portions of a test panel in fixed position;
a loading head assembly operable to impart a load to a first major face of a test panel between the retained opposite end portions of the panel;
a load transfer assembly operable to mechanically couple at least one dead weight to the loading head assembly for load transfer therebetween;
a sensor for measuring magnitude of deflection of the panel from an applied load and generating a signal indicative of the magnitude of panel deflection;
a mobile loading platform assembly comprising
a reciprocally vertically-movable platform for supporting the at least one dead weight,
a linear actuator assembly comprising a motor controller and a linear actuator having an output shaft mechanically coupled to the platform, wherein the linear actuator assembly is operable to vertically move the platform at a controlled rate effective to load the load transfer assembly at a uniform rate with a progressively increasing amount of weight of the dead weight until the dead weight is fully transferred to the load transfer assembly and unsupported by the platform,
a load cell for developing and transmitting load-indicating signals corresponding to amount of weight of the dead weight supported by the platform;
a computerized control system operable to
control actuation of the linear actuator assembly effective to control starting/stopping movement of the output shaft of the linear actuator, and
receive and store the panel deflection signals and platform load-indicating signals and corresponding measurement times during initial loading of the load transfer assembly with the dead weight and during constant load conditions maintained thereafter for a period of time.

2. A panel performance testing system of claim 1, wherein computerized control system includes at least one input device and a central processing unit, and said computerized control system is operable for storing and executing a programmable load/deflection measuring program for performing a creep test on a panel.

3. A panel performance testing system of claim 1, wherein the computerized control system is operatively coupled to i) the motor controller for controlling starting and stopping translation of the output shaft of the linear actuator, and ii) said load cell and deflection sensor for receiving, recording and processing data relating to the applied load and the corresponding panel deflection, respectively, as a function of time during an initial loading period and a subsequent creep cycle testing period, and said computerized control system being operable to process the recorded test data to compute a measure of the creep of the panel.

4. A panel performance testing system of claim 1, wherein the motor controller is operable to control the rate of weight loading to a constant value between 0.005 to 5 inch per minute until the weight is fully suspended from the cable and unsupported by the platform.

5. A panel performance testing system of claim 1, wherein the mobile loading platform assembly further comprises a lift truck frame supporting the platform, the linear actuator, the computerized control system, and wheels for controlled movement of the lift truck frame towards and away from the test panel support frame assembly.

6. A panel performance testing system of claim 1, wherein the load head assembly comprises two rectilinear contact rods for applying load to the first major face of a test panel along two parallel lines of contact made by the respective rods along their lengths with the first major face.

7. A panel performance testing system of claim 1, wherein the linear actuator comprises a roller screw and rolling elements operably connected to a rotary power transmission source and the output shaft.

8. A panel performance testing system of claim 1, wherein the linear actuator comprises multiple threaded helical rollers assembled in a planetary arrangement around a portion of the output shaft comprising a threaded shaft, wherein the linear actuator converts rotary motion into linear movement of the threaded shaft.

9. A panel performance testing system of claim 8, further comprising a constant power transmission to power the linear actuator and a position feedback assembly operable to generate signals corresponding to the position and velocity of the output shaft of the linear actuator.

10. A panel performance testing system of claim 1, wherein the load transfer assembly comprises a pulley and cable, in combination, wherein the cable is operable for connecting the loading head assembly and dead weight, and the pulley includes a freely rotatable surface over which the cable may translate in a guided manner.

11. The panel testing device of claim 1, wherein the panel deflection sensor comprises an end portion supporting a deflection sensor, wherein the end portion being movable between a non-testing position where the sensor is out of contact with the panel and a test position where the sensor is in contact with the panel when the deflection sensor is in the test position operable to measure a deflection of the panel.

12. The panel performance system of claim 1, further comprising a computer monitor coupled in communication with the computerized control system, and operable to display panel test results.

13. The panel performance system of claim 1, wherein the deflection sensor is operable to output a signal indicative of panel deflection that is received at the computerized control system via wireless communication.

14. A method for testing a panel of material, comprising:
(A) providing a panel performance testing system comprising
  a panel testing support frame assembly comprising first and second retaining assemblies for releasably retaining opposite end portions of a test panel in fixed position;
  a loading head assembly operable to impart a load to a first major face of a test panel between the retained opposite end portions of the panel;
  a load transfer assembly operable to mechanically couple at least one dead weight to the loading head for load transfer therebetween;
  a sensor for measuring magnitude of deflection of the panel from an applied load and generating a signal indicative of the magnitude of panel deflection;
  a mobile loading platform assembly comprising
    a reciprocally vertically-movable platform for supporting the at least one dead weight,
    a linear actuator assembly comprising a motor controller and a linear actuator having an output shaft mechanically coupled to the platform, wherein the linear actuator assembly is operable to vertically move the platform at a controlled rate effective to load the load transfer assembly at a uniform rate with a progressively increasing amount of weight of the dead weight until the dead weight is fully transferred to the load transfer assembly and unsupported by the platform,
    a load cell for developing and transmitting load-indicating signals corresponding to amount of weight of the dead weight supported by the platform;
    a computerized control system operable to
      control actuation of the linear actuator assembly effective to control starting/stopping movement of the output shaft of the linear actuator, and
      receive and record the panel deflection signals and platform load-indicating signals and corresponding measurement times during initial loading of the load transfer assembly with the dead weight and during constant load conditions maintained thereafter for a period of time;
(B) immobilizing opposite ends of a test panel in the panel testing support frame with the retaining assemblies;
(C) powering the linear actuator assembly in response to a starting command of the computerized control system effective to lower the support platform effective to load the load transfer assembly at a uniform rate with a progressively increasing amount of weight of the dead weight until the dead weight is fully suspended from the cable and unsupported by the platform;
(D) maintaining, after step (C), the test panel under constant load for a given time period;
(E) acquiring, during steps (C) and (D), panel deflection signals and platform load-indicating signals and corresponding measurement times at the computerized control system;
(F) processing, at said computerized control system, said load-indicating signals and said deflection-indicating signals for deriving test results comprising the applied load, the deflection of the panel and corresponding measurement times.

15. The method of claim 14, wherein said deriving further includes calculating creep rate of the test panel.

16. The method of claim 14, comprising saving the test results in a data file format in the computerized control system.

17. The method of claim 14, wherein the test results are displayed on a computer monitor operatively coupled with the computerized control system.

18. The method of claim 14, wherein the deflection sensor outputs a signal indicative of panel deflection that is received at the computerized control system via wireless communication.

19. The method of claim 14, comprising determining panel creep rate of the test panel with the panel performance testing system in accordance with ASTM D6815-02a.

20. The method of claim 14, further comprising initially loading a plurality of different test panels supported on different respective test frames at different respective test stations located in the same test room by shuttling the same mobile platform assembly to successive different test stations after completing initial loading and while being absent during the constant stress portion of a creep test cycle as performed on a test panel at a previous test station.

* * * * *